United States Patent
Stupp et al.

(10) Patent No.: US 7,371,887 B2
(45) Date of Patent: May 13, 2008

(54) OLIGO(P-PHENYLENE VINYLENE) AMPHIPHILES AND METHODS FOR SELF-ASSEMBLY

(75) Inventors: Samuel I. Stupp, Chicago, IL (US); James F. Hulvat, Chicago, IL (US); Marina Sofos, Evanston, IL (US); Keisuke Tajima, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 11/005,558

(22) Filed: Dec. 6, 2004

(65) Prior Publication Data

US 2005/0214952 A1 Sep. 29, 2005

Related U.S. Application Data

(60) Provisional application No. 60/527,047, filed on Dec. 4, 2003.

(51) Int. Cl.
*C07C 69/76* (2006.01)
*C07C 217/54* (2006.01)
*C07C 43/215* (2006.01)
*H01L 21/00* (2006.01)

(52) U.S. Cl. .......................... 560/57; 560/64; 564/156; 564/171; 564/181; 564/183; 564/186; 564/283; 564/285; 564/286; 564/287; 564/288; 564/290; 568/609; 568/640; 568/646; 252/299.6

(58) Field of Classification Search ............... 568/609, 568/640, 646; 560/57, 64; 564/283, 288, 564/290, 156, 171, 181, 183, 186, 285, 286, 564/287; 252/299.01, 299.6

See application file for complete search history.

(56) References Cited

U.S. PATENT DOCUMENTS 4,314,820 A * 2/1982 Weber et al. ................. 8/648

OTHER PUBLICATIONS

Sun et al., Blue emitting diodes based on self-assembled multilayers of cationic oligo(p-phenylene vinylene) and sulfonated polyaniline, May 1999, Materials Science and Engineering C10 (1-2), pp. 83-86.*

Sun et al., "Blue emitting diodes based on self-assembled multilayers of cationic oligo(p-phenylene Vinylene) and sulfonated polyaniline". Materials Sciences and Engineering. May 1999, C10 (1-2), pp. 83-86, especially p. 84.

Tao et al., "Luminescence properties of end-substituted oligo(phenylenevinylene)s". Synthetic Metals. Jun. 2000, vol. 111-112, p. 417-420, especially p. 418.

Cacialli et al., "Synthesis and characterization of poly(distyrylbenzene-block-hexa(ethylene oxide) and its fluorinated analogue-two new block copolymers and their application in electroluminescent devices". Polymer. Jun. 2002, vol. 43, No. 12, pp. 3555-3561, especially p. 3558.

* cited by examiner

*Primary Examiner*—Rosalynd Keys
(74) *Attorney, Agent, or Firm*—Reinhart Boerner Van Deuren SC

(57) ABSTRACT

Amphiphilic oligo(p-phenylene vinylene) compounds and methods of use en route to self-assembled composites and device fabrication.

25 Claims, 2 Drawing Sheets

III  a: n = 2  b: n = 3
c: n = 4  d: n = 6

OLIGO(P-PHENYLENE VINYLENE) AMPHIPHILES AND METHODS FOR SELF-ASSEMBLY

This application claims priority benefit from application Ser. No. 60/527,047 filed Dec. 4, 2003, the entirety of which is incorporated herein by reference.

The United States government has certain rights to this invention pursuant to Grant No. DE-FG02-00ER45810 from the Department of Energy to Northwestern University.

BACKGROUND OF THE INVENTION

Previous research efforts have led to the synthesis of many conjugated polymers, particularly derivatives of poly(phenylene vinylene) (PPV), soluble in organic solvents and easily processed into films with great promise as organic electronic materials. π-Conjugated oligomers, first investigated as model compounds for conjugated polymers, are now widely studied for use in optoelectronic devices because their well-defined chemical structure facilitates tuning of electronic properties. Use of well-defined oligomers reduces defect density while enabling more control over the effective conjugation length. In particular, oligo(p-phenylene vinylene)s (OPVs) are being investigated for use in solar cells and light emitting diodes (LEDs) due to their stability, high luminescent efficiency and ease of synthesis. OPVs with solubilizing substituents combine the low-cost, solution-based processing of conjugated polymers with the improved structural control inherent to oligomers.

Controlling the nanoscale structure of rod-like conjugated polymers has proven difficult. Supramolecular order plays a critical role in device performance, as both charge mobility and luminescent efficiency are influenced by molecular aggregation and structural defects. One approach to control nanostructure has been to design polymers that could exhibit thermotropic or lyotropic liquid crystalline (LC) behavior. Among these are the "hairy-rod" type liquid crystalline polymers (LCPs), in which flexible alkyl side chains added for solubility induce nanophase separation of the rigid, conjugated polymer backbone. A more direct approach is to incorporate calamitic mesogens as side chains on a conjugated polymer backbone. Both methods can result in layered, smectic ordering of the polymer, but only micron-sized domains are generally obtained due to the viscosity and rigidity of the polymer's extended backbone conjugation, which inhibits formation of the large monodomains needed in device applications.

Use of conjugated, liquid crystalline oligomers can improve ordering, and several LC oligomers based on substituted OPV rods have been reported. Many are analogs of conjugated LCPs, with flexible alkyl chains grafted laterally onto the molecule. However, such substituent configurations transverse to a longitudinal molecular axis introduce bulky, sterically hindering groups that disrupt co-planarity within the π-conjugated system.

SUMMARY OF THE INVENTION

Accordingly, it is an object of the present invention to provide OPV compounds and/or methods for assembly, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide an amphiphilic OPV compound without resort to hydrophobic and/or hydrophilic components transverse to the OPV molecular axis, and without introducing an element of steric hindrance for disruption of co-planarity within the conjugated system. It can be another object of the present invention to provide OPV amphiphiles end-substituted, symmetrically or asymmetrically, for self-assembly under a range of fabrication conditions.

Other objects, features, benefits and advantages of the present invention will be apparent from this summary and its descriptions of certain embodiments, and will be readily apparent to those skilled in the art having knowledge of various electro-optic compounds, compositions, components and/or devices. Such objects, features, benefits and advantages will be apparent from the above as taken into conjunction with the accompanying examples, data, figures and all reasonable inferences to be drawn therefrom.

The present invention relates to OPV amphiphiles, either asymmetrically hydrophobic and hydrophilic end-substituted and comprising a triblock configuration, or end-substituted with combined hydrophobic/hydrophilic moieties. Accordingly, in part, this invention comprises compounds of a formula

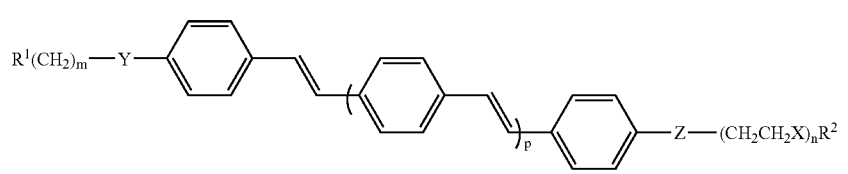

(I)

wherein X can be selected from O and $CH_2$, and $R^1$ and $R^2$ can be independently selected from H and alkyl moieties where X is O, and $R^1$ and $R^2$ can be quaternary ammonium salt moieties where X is $CH_2$, Y and Z can be independently selected from O, NH, C(O)O and C(O)NH; n can be an integer ranging from 2 to about 50; m can be an integer ranging from 2 to about 20; and p can be an integer ranging from 1 to about 4.

With regard to asymmetric compounds

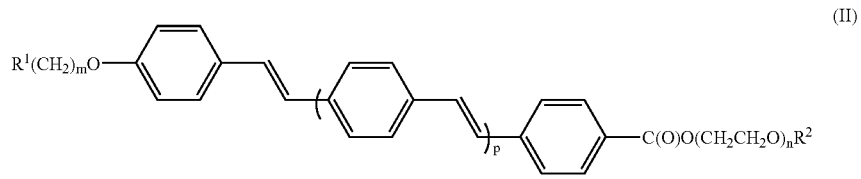

(II)

such amphiphiles can form lyotropic and thermotropic LC phases in polar solvents, and the solubility and mesophase structure can be tuned by controlling the length of a hydrophilic (e.g., a poly (ethylene glycol) (PEG)) block. With a sufficiently long PEG, OPV amphiphiles become water soluble, a significant advantage for large scale processing of materials. With such nonionic amphiphiles of this invention, liquid crystallinity can be used to control OPV aggregation, influencing exciton mobility, fluorescence, and potentially leading to improved charge carrier mobility in heterojunction solar cells or enabling more efficient, polarized emission from organic light emitting diodes (OLEDs).

With regard to the end-charged, hydrophobic/hydrophilic substituted compounds

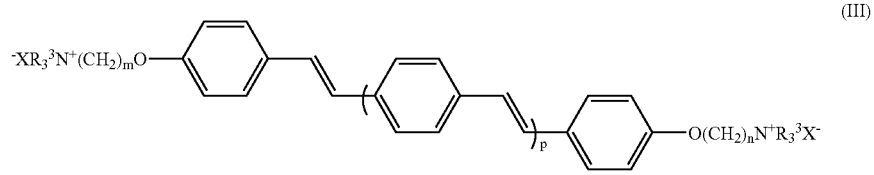

(III)

such amphiphiles, regardless of symmetry (e.g., n≠m), can be used as templates for sol-gel synthesis of nanostructured materials, optionally in the presence of inorganic precursors. For example, condensation of such an OPV amphiphile with a silicate induces formation of a periodic bilayer structure upon solvent evaporation. Such self-assembly can be used for deposition of OPV compounds and compositions in the fabrication nanostructured OLEDs.

DETAILED DESCRIPTION OF CERTAIN EMBODIMENTS

Syntheses of several asymmetric OPV amphiphiles II are shown in Scheme 1 and described more fully, below, in the following examples. In a representative synthesis, the conjugated vinylene bond was formed using the Horner-Emmons reaction between phosphonate 3 and aldehyde 4 at a low temperature to obtain trans-phenylene vinylene 5.

Scheme 1.
Synthesis of an asymetric OPV Amphiphile

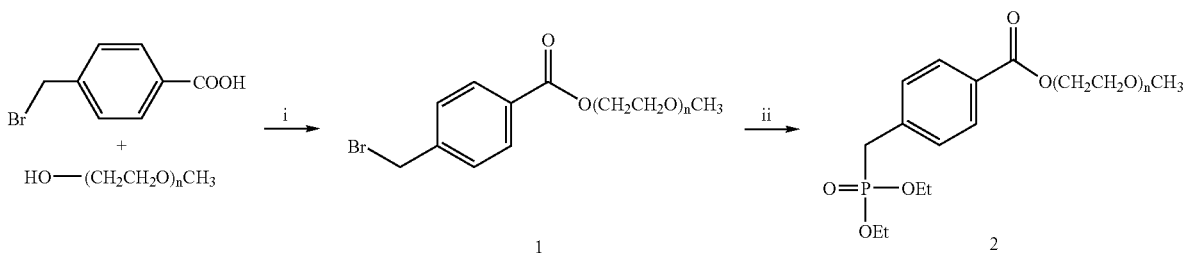

-continued

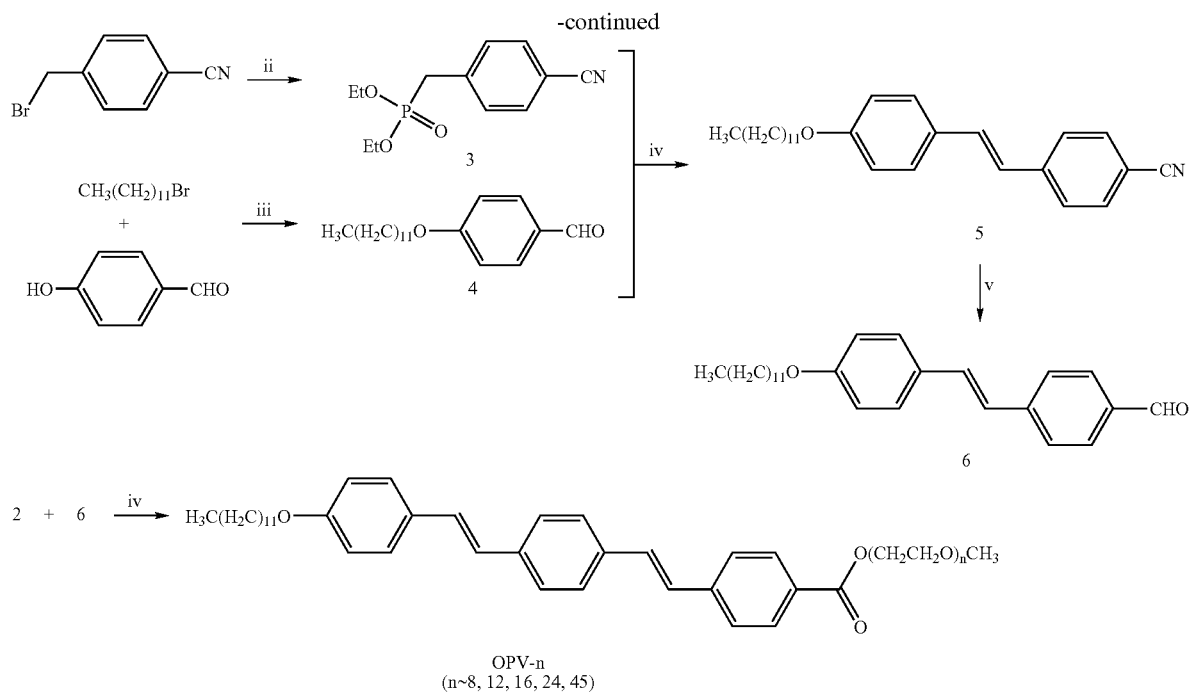

OPV-n
(n~8, 12, 16, 24, 45)

Reaction conditions:
i) DPTS/EDIC, CH$_2$Cl$_2$
ii) P(OEt)$_3$, 130° C.
iii) K$_2$CO$_3$, 18-crown-6, acteone, 56° C.
iv) LDA, cyclohexane/THF, -78° C.
v) DIBAL-H, Et$_2$O, 0° C.

Aldehyde 6 was obtained by reduction of the cyano group in 5 with diisobutylaluminum hydride. To avoid solubility problems with unsubstituted OPV, the coupling reaction of PEG-phosphonate 2 and aldehyde 6 can be provided as the last step. For purpose of illustration, while the length of the OPV segment and alkyl tail were kept constant, the PEG block was varied from an average of about 8 to about 45 repeat units (OPV-8, -12, -16, etc.) in order to study its effect on mesophase behavior (PEG M$_w$=350 to 2000 g/mol, M$_w$/M$_n$=1.02). As discussed above, however, length of both the OPV and hydrophobic components can also be independently varied depending upon synthetic route or fabrication system, or to meet a particular end use application.

OPV amphiphiles III can be synthesized using an analogous Horner-Emmons reaction for the formation of trans-vinyl bonds and subsequent alkylation of tertiary amines to quaternary ammonium salts. (See, the following examples) Like compounds II, these molecules have rigid OPV segments expected to aggregate as a result of hydrophobic and π-π interactions. With reference to FIG. 3, compound IIIa (n=2) is readily soluble in MeOH, while compounds IIIb-d with longer alkyl moieties are less soluble.

With reference to compound (I), other embodiments of this invention corresponding to compounds (II) or (III) can be prepared consistent with the procedures described in Scheme 1 or straight-forward modifications thereof as would be understood in the art. For example, X can be CH$_2$ through use of a fatty alcohol in reaction i. Likewise, R$^2$ can be H using a di-hydroxy PEG component. Y can be NH through use of an amino-substituted benzaldehyde reaction iii; and Z can be C(O)N using an amino-terminated PEG component in reaction i. Regardless, for any of compounds (I)-(III), p can vary in number upon repetitious use of a phosphonate such as 3 and a benzaldeyhyde such as 6 (e.g., reactions iv and v). Further, one or more positions on any or all of the phenylene moieties can be substituted, optionally with one or more electron withdrawing groups, through use of corresponding phenyl starting material(s). Likewise, vinylidene substitution, optionally with one or more electron donating groups, can be effected through Horner-Emmons type chemistry using appropriate ketone and/or benzyl reagent(s), such substitutions as would be understood by those skilled in the art of OPV synthesis and related device application.

EXAMPLES OF THE INVENTION

Figure 1:
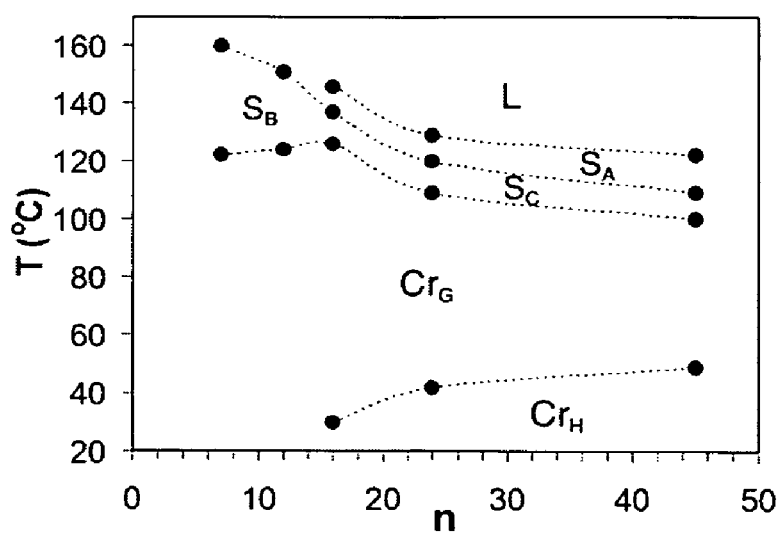
FIG. 1 shows a phase diagram of transitions observed in DSC as a function of PEG length, with preliminary phase assignments.

With regard to examples 1-9: Melting and mesophase transition temperatures were determined using a TA Instruments 2920 DSC/TGA. 10 mg samples were placed in hermetically sealed Al pans and cycled three times at 5° C. min$^{-1}$. Transition temperatures were determined from the second heating cycle (all were fully reversible). Thermogravimetric analysis (TGA) showed an onset of decomposition at 190° C. on heating at 10° C. min$^{-1}$ in air, which was well above the clearing temperature for all OPV-amphiphiles investigated. Additionally, the stability of the molecule against thermal degradation was verified by NMR, which showed no change after heating the molecule to 180° C. for 4 hr. in air. Purity and polydispersity of the final product was determined using a Waters 2690 GPC in THF calibrated with polystyrene standards. A single peak was obtained for each amphiphile. POM was performed using a Leitz Laborlux 12POL polarizing microscope with a thermostatically controlled heating stage and a 35 mm film camera. Samples were sealed with a 75 μm spacer between pre-cleaned glass slides, heated to isotropization and then cooled at 0.3° C. min$^{-1}$ to obtain identifiable LC textures. SAXS spectra were collected on samples sealed in quartz capillary tubes using a Rigaku $Cu_{K\alpha}$ source at 33 kV and a 2D Bruker CCD detector calibrated with silver behenate. Wide angle powder X-ray diffraction patterns were collected on a Scintag XDS2000 automated diffractometer with a $Cu_{K\alpha}$ source operating at 40 kV. UV-vis absorption was studied using a Cary 500 UV-VIS-NIR spectrometer operating in double beam mode. PL spectra were collected on a PC1 Spectrofluorimeter in right angle geometry. Both instruments were fitted with heated, thermostatically controlled sample holders. For film measurements, 1 wt % solutions were spin-coated at 2000 rpm on quartz plates, yielding films 300 nm thick. For PL, film samples were placed at 45° to the detector. The excitation wavelength was chosen at the absorption maximum from UV-vis, but PL spectral shape was found to be relatively insensitive to excitation wavelength. Dilute solutions for fluorescence in THF were prepared by adjusting the concentration to an absorption of <0.1. For high concentration solutions and LC gels, ultrashort (10 μm) path length quartz holders were used to allow adequate transparency. To ensure complete dissolution of the OPV amphiphile, lyotropic LC gels were prepared by dissolving the material at 10 wt % and then evaporating solvent to achieve the desired concentration. Samples were then heated in sealed vials to homogenize. HPLC grade solvents for LC experiments (THF, $CH_3CH$, DMSO) were degassed prior to use, and DI water was purified using a Millipore filtration system.

Example 1

The OPV-8 amphiphile, illustrating an embodiment of compound II, was synthesized by the following procedures (1a-1g). Other OPV-n amphiphiles were synthesized by a similar procedure beginning with longer poly(ethylene glycol)methyl ethers. Unless otherwise noted, all starting materials were obtained from commercial suppliers and used without further purification. 4-(Dimethylamino)-pyridinium-4-toluenesulfonate (DPTS) was prepared according to literature. (Granier, T.; Thomas, E. L.; Gagnon, D. R.; Karasz, F. E.; Lenz, R. W. *J. Polym. Sci. Part B: Polym. Phys.* 1986, 24, 2793-2804.) The $^1$H NMR and $^{13}$C NMR spectra were recorded on a Varian Unity 400 (400 MHz) or Unity 500 (500 MHz) spectrometer using the solvent proton signal as standard. Mass spectra were obtained on a Micromass Quattro II atmospheric pressure ionization (API) triple quadrupole mass spectrometer. Matrix-assisted laser desorption ionization-time of flight mass spectrometry (MALDI-TOF MS) was performed on an Applied Biosystems Voyager-DE Pro. Silica for flash chromatography was ICN Silitech 32-63 D 60 A.

Example 1a

Poly(ethylene glycol)methyl ether-4-bromomethyl benzoate (1). α-Bromo-p-toluic acid (1.07 g, 5.00 mmol, 1.00 equiv.), poly(ethylene glycol) methyl ether ($M_w$=350 g/mol, 1.75 g, 5.00 mmol, 1.00 equiv.), DPTS (1.56 g, 5.30 mmol, 1.06 equiv.), and $CH_2Cl_2$ (150 ml) were all combined in a flask with a stirring bar. 1-(3-(Dimethylamino)propyl)-3-ethylcarbodiimide hydrochloride (1.44 g, 7.53 mmol, 1.50 equiv.) was added and the reaction mixture was stirred for 24 h at room temperature. The solution was washed with 5% aqueous solution of citric acid, and saturated aqueous solution of NaCl. The organic layer was collected, dried with $MgSO_4$, filtered, and concentrated in vacuo. The product was subjected to a column chromatography using 5% $MeOH/CH_2Cl_2$ as the eluant to afford the product (2.2 g, 4.0 mmol, 80% yield).
$^1$H NMR (400 MHz, $CDCl_3$) δ: 8.06 (d, 2H, J=7.9 Hz), 7.47 (d, 2H, J=8.6 Hz), 4.63 (s, 2H), 4.50 (t, 2H, J=4.9 Hz), 3.85 (t, 2H, J=4.6 Hz), 3.67 (m, 24H), 3.39 (s, 3H); $^{13}$C NMR (500 MHz, $CDCl_3$) δ: 166.0, 142.8, 130.4, 130.2, 129.0, 72.5, 71.9, 70.7, 70.6, 70.5, 70.2, 64.3, 61.6, 59.0, 32.3.

Example 1b

Poly(ethylene glycol)methyl ether-4-((diethylphosphono)methyl) benzoate (2). Benzyl bromide 1 (1.0 g, 2.1 mmol, 1.0 equiv.) and triethyl phosphite (0.72 mL, 4.2 mmol, 2.0 equiv.) were placed in a flask with a magnetic stirring bar. A distillation apparatus was attached to collect ethyl bromide formed along with the reaction. The mixture was immersed in an oil bath and heated to 130° C. for 24 h. The reaction mixture was cooled, diluted with $Et_2O$, and washed with $H_2O$. The organic layer was dried with $MgSO_4$, filtered, and concentrated in vacuo. The resulting oil (1.29 g, 2.10 mmol, 100% yield) was used for the next Horner-Emmons reaction without further purification. $^1$H NMR (400 MHz, $CDCl_3$) δ: 8.00 (d, 2H, J=7.9 Hz), 7.37 (d, 2H, J=7.3 Hz), 4.45 (t, 2H, J=4.9 Hz), 4.01 (t, 2H, J=6.7 Hz), 3.63 (m, 24H), 3.19 (d, 2H, J=22.0 Hz).

Example 1c

Diethyl-4-cyanobenzyl phosphonate (3). Compound 3 was prepared with α-bromo-p-tolunitrile (10 g, 51 mmol, 1.0 equiv.) and triethyl phosphite (9.6 mL, 56 mmol, 1.1 equiv.) via Arbuzov condition similar to the reaction for 1 as colorless oil (12.9 g, 51.0 mmol 100% yield). $^1$H NMR (400 MHz, $CDCl_3$) δ: 7.60 (d, 2H, J=7.9 Hz), 7.41 (d, 2H, J=7.9 Hz), 4.03 (m, 4H), 3.19 (d, 2H, J=22.6 Hz), 1.25 (t, 6H, J=7.0 Hz).

Example 1d

4-Dodecyloxybenzaldehyde (4). 4-Hydroxybenzaldehyde (5.0 g, 41 mmol, 1.0 equiv.), potassium carbonate (8.5 g, 61 mmol, 1.5 equiv.), dodecyl bromide (12.3 g, 49.2 mmol, 1.20 equiv.), and 18-crown-6 (1.0 g, 4.1 mmol, 0.10 equiv.) were placed in a flask with a magnetic stirring bar and a cooling column, and dissolved in 50 ml of acetone. The mixture was refluxed for 24 h. After cooling down, the mixture was filtered and concentrated in vacuo. The crude product was subjected to a column chromatography using $CH_2Cl_2$ to afford the product as pale yellow solid (10.3 g, 35.0 mmol, 87% yield). $^1$H NMR (400 MHz, $CDCl_3$) δ: 9.85 (s, 1H), 7.83 (d, 2H, J=8.6 Hz), 7.00 (d, 2H, J=8.6 Hz), 4.05

(t, 2H, J=6.4 Hz), 1.80 (m, 2H), 1.27 (m, 18H), 0.89 (t, 3H, J=6.7 Hz); $^{13}$C NMR (500 MHz, CDCl$_3$) δ: 191.0, 164.5, 132.2, 130.0, 115.0, 68.7, 32.2, 29.9, 29.8, 29.6, 29.3, 26.2, 22.9, 14.4; APCI-MS m/z 291.3 (M$^+$).

Example 1e 4-(2-(4-Dodecyloxyphenyl)-(E)-1-ethenyl)-1-benzonitrile (5). Lithium diisopropylamide mono(tetrahydrofuran) (LDA) (1.5 M solution in cyclohexane, 28.3 mL, 42.5 mmol, 1.20 equiv.) and 50 mL of THF were placed in a dry flask using a magnetic stirring bar under N$_2$ and cooled to −78° C. Phosphonate 3 (9.0 g, 35 mmol, 1.0 equiv.) dissolved in 50 mL of THF was added dropwise into the precooled solution with a dropping funnel. The reaction mixture was placed in a 0° C. ice bath and the aldehyde 4 (10.3 g, 35.4 mmol, 1.00 equiv.) dissolved in 50 mL of THF solution was added dropwise into the mixture. The reaction mixture was stirred overnight at room temperature, and quenched by adding aqueous solution of acetic acid. THF was removed by evaporation and yellowish white solid precipitated out in the water layer was collected by filtration. The crude product was subjected to a column chromatography using CH$_2$Cl$_2$ to afford the product as pale yellow solid (10.9 g, 28.0 mmol, 79% yield). $^1$H NMR (400 MHz, CDCl$_3$) δ: 7.61 (d, 2H, J=8.5 Hz), 7.54 (d, 2H, J=7.9 Hz), 7.46 (d, 2H, J=8.5 Hz), 7.16 (d, 1H, J=16.5 Hz), 6.94 (d, 1H, J=16.5 Hz), 6.90 (d, 2H, J=8.6 Hz), 3.98 (t, 2H, J=6.4 Hz), 1.79 (m, 2H), 1.45 (m, 2H), 1.26 (m, 16H), 0.88 (t, 3H, J=6.7 Hz); $^{13}$C NMR (500 MHz, CDCl$_3$) δ: 160.0, 142.5, 132.7, 132.3, 128.5, 127.3, 126.8, 124.6, 119.4, 115, 1, 114.8, 68.4, 32.2, 29.9, 29.7, 29.6, 29.5, 26.3, 22.9, 14.4; APCI-MS m/z 390.5 (M$^+$).

Example 1f 4-(2-(4-dodecyloxyphenyl)-(E)-1-ethenyl)-1-benzaldehyde (6). Nitrile 5 (10.6 g, 36.8 mmol, 1.00 equiv.) was dissolved in 500 mL of Et$_2$O and cooled to 0° C. Diisobutylaluminum hydride (1.0 M solution in hexane, 55.2 mL, 55.2 mmol, 1.50 equiv.) was added dropwise into the solution using a dropping funnel. The solution was stirred at 0° C. for 20 min and poured into 10% AcOH/H$_2$O (500 mL). The ether layer was evaporated in vacuo and a yellow solid precipitated out in the water layer was collected by filtration. The crude product was subjected to a column chromatography using CH$_2$Cl$_2$ to afford the product as yellow solid (8.4 g, 21 mmol, 58% yield). $^1$H NMR (400 MHz, CDCl$_3$) δ: 9.98 (s, 1H), 7.85 (d, 2H, J=7.9 Hz), 7.62 (d, 2H, J=7.9 Hz), 7.48 (d, 2H, J=8.6 Hz), 7.22 (d, 1H, J=16.5 Hz), 7.00 (d, 1H, J=16.5 Hz), 6.91 (d, 2H, J=8.6 Hz), 3.98 (t, 2H, J=6.7 Hz), 1.79 (m, 2H), 1.45 (m, 2H), 1.26 (m, 16H), 0.88 (t, 3H, J=6.7 Hz); $^{13}$C NMR (500 MHz, CDCl$_3$) δ: 191.9, 159.9, 144.2, 135.2, 132.1, 130.5, 129.3, 128.5, 126.8, 125.2, 115.1, 68.4, 32.2, 29.9, 29.7, 29.6, 29.5, 26.3, 22.9, 14.4; APCI-MS m/z 393.4 (M$^+$).

Example 1g (Poly(ethylene glycol)methyl ether)-4-(2-(4-(2-(4-dodecyloxyphenyl)-(E)-1-ethenyl)-phenyl)-(E)-1-ethenyl)-1-benzoate (OPV-8). OPV-8 amphiphile was prepared with aldehyde 6 (0.36 g, 0.92 mmol, 1.0 equiv.), phosphonate 2 (0.5 g, 0.9 mmol, 1 equiv.) and LDA (1.5 M solution in cyclohexane, 0.74 mL, 1.1 mmol, 1.2 equiv.) via the Horner-Emmons condition similar to the reaction for compound 5. The crude product was extracted with CH$_2$Cl$_2$ and subjected to a column chromatography using 5% MeOH/CH$_2$Cl$_2$ to afford the product as yellow solid (0.56 g, 0.66 mmol, 72% yield). $M_w/M_n$=1.01. MALDI-TOF MS m/z 900.2 (M+Na$^+$). $^1$H NMR (400 MHz, CDCl$_3$) δ: 8.05 (d, 2H, J=8.6 Hz), 7.58 (d, 2H, J=8.6 Hz), 7.52 (d, 4H, J=3.1 Hz), 7.46 (d, 2H, J=8.5 Hz), 7.23 (d, 1H, J=16.5 Hz), 7.14 (d, 1H, J=16.5 Hz), 7.11 (d, 1H, J=16.5 Hz), 6.98 (d, 1H, J=16.5 Hz), 6.91 (d, 2H, J=8.6 Hz), 4.45 (t, 2H, J=4.5 Hz), 3.99 (t, 2H, J=6.7 Hz), 3.85 (t, 2H, J=4.6 Hz), 3.65 (m, 24H), 1.79 (m, 2H), 1.45 (m, 2H), 1.27 (m, 16H), 0.89 (t, 3H, J=6.7 Hz); $^{13}$C NMR (500 MHz, CDCl$_3$) δ: 166.5, 159.3, 142.2, 138.0, 135.8, 131.1, 130.4, 130.0, 129.0, 128.9, 128.0, 127.4, 127.3, 126.8, 126.5, 126.0, 114.9, 72.1, 70.9, 70.8, 69.5, 68.3, 64.3, 59.2, 32.1, 29.9, 29.8, 29.6, 29.6, 29.5, 26.3, 22.9, 14.4.

Example 2

The OPV amphiphiles synthesized were found to be thermotropic LCs with mesophase structure highly dependent on the length of the PEG block. Below OPV-16, the molecules form liquid crystals at room temperature. As the length of the hydrophilic block increases the PEG crystallizes and the thermal range of the mesophase narrows. Table 1 summarizes the molecular weight and thermal transitions observed for each amphiphile. Transition temperatures were determined from differential scanning calorimetry (DSC).

TABLE 1

LC Mesophase Transitions Observed for OPV Amphiphiles

| OPV-n[a] | $M_w$ (g/mol)[b] | $M_w/M_n$[c] | $T_m$ (° C.) | $T_{LC}$ (° C.)[d] | $T_c$ (° C.)[e] |
|---|---|---|---|---|---|
| OPV-8 | 350 | 1.01 | <RT | 122 | 160 |
| OPV-12 | 550 | 1.02 | <RT | 124 | 151 |
| OPV-16 | 750 | 1.02 | 30 | 126, 137 | 146 |
| OPV-24 | 1100 | 1.03 | 42 | 109, 120 | 131 |
| OPV-45 | 2000 | 1.02 | 49 | 100, 109 | 123 |

[a]n = average number of repeat units in PEG blocks.
[b]Average molecular weight of PEG block.
[c]Polydispersity of OPV-amphiphiles (determined by GPC).
[d]Liquid crystalline mesophase transition(s).
[e]Clearing temperature of LC phase.

Example 3a

Small angle X-ray scattering (SAXS) indicates a smectic structure for all the amphiphiles studied. Small and wide angle X-ray diffraction patterns for the OPV-amphiphiles show the interlayer spacing is approximately equal to the fully extended lengths of the molecules, indicating significant interdigitation and/or tilt within a bilayer smectic structure. The higher order peaks observed between 2°-4° 2θ disappear with longer PEG chains, as does the sharp wide angle peak at 4.3 angstroms, which is likely to correspond to the break up of OPV ordering within the smectic layers. Two other peaks appear at 4.6 and 3.8 angstroms, which may arise from the crystal structure of the PEG block as these peaks were also observed in control PEG-alkyl diblock molecules without OPV. The X-ray data indicate that at room temperature OPV-amphiphiles with short PEG chains form an interdigitated bilayer smectic phase with a highly ordered OPV layer. As the length of the hydrophilic segment increases, PEG crystallization disrupts the OPV layer, resulting in a less ordered structure.

Example 3b

The OPV amphiphiles show distinctive, strongly birefringent mesophase textures when analyzed by polarized optical microscopy (POM). These textures were compared with in the literature, however the similarities among higher ordered smectic phases and the complexity of the bilayer structure needed further characterization for structural determination. In FIG. 1, preliminary phase assignments are proposed for the OPV layer of the LC, based on X-ray and DSC results as well as POM textures.

Figure 2:
FIG. 2 shows mosaic birefringence texture of the OPV-12 amphiphile at 130° C., observed between crossed polarizers.

The competing influence of the OPV and PEG segments on amphiphile aggregation is clear from the phase diagram. A distinct transition occurs above OPV-12 as the size of the hydrophilic PEG exceeds that of the hydrophobe (MW=494 g/mol for the alkyl-OPV). FIG. 2 shows a mosaic birefringence texture, similar to that of the smectic B ($S_B$) mesophase, observed for shorter PEG lengths.

Example 3c

Here $S_B$ ordering may be driven by OPV aggregation, while less ordered smectic C ($S_C$) and smectic A ($S_A$) phases result when longer PEG blocks frustrate order within the OPV sublayers. At lower temperatures, a texture similar to the crystalline smectic G ($Cr_G$) mesophase is observed, in which OPV molecules are hexagonally ordered in crystal-like layers with positional and orientational order, but retaining the rotational and diffusional motion of a liquid. In longer OPV amphiphiles at room temperature, crystallization of the hydrophilic PEG block inhibits molecular rotation, as occurs in the transition from the $Cr_G$ to the $Cr_H$ mesophase. While this transition increases ordering of the hydrophilic sublayer, crystallization of the PEG block may actually disrupt packing in the OPV sublayers, due to differences in the preferred packing arrangement of the two segments. This disruption of the OPV sublayer should be evident in the spectroscopic behavior of the OPV-amphiphiles.

Example 4a

The structural characterization of these systems demonstrates how variation in PEG length can change the aggregation state of OPV segments. This relationship can be used to influence the optical and electronic properties of these materials to a greater extent than is possible with standard solution-based processing of OPVs. Thus, UV-vis absorption and photoluminescence (PL) spectroscopy were used to investigate the effect of PEG length on OPV aggregation in solutions and in thin films (Table 2).

TABLE 2

UV-vis Absorption and Photoluminescence (PL) of OPV-Amphiphiles

| | $\lambda_{abs}$ (nm)[a] THF soln. | $\lambda_{PL}$ (nm)[b] THF soln. | $\lambda_{abs}$ (nm)[c] THF film | $\lambda_{PL}$ (nm)[d] THF film | $\lambda_{PL}$ (nm)[e] $CH_3CN$ film |
|---|---|---|---|---|---|
| OPV-8 | 375 | 467 | 308 | 510 | 508 |
| OPV-12 | 377 | 467 | 309 | 508 | 507 |
| OPV-16 | 375 | 466 | 320 | 508 | 504 |
| OPV-24 | 376 | 468 | 322 | 506 | 468 |
| OPX-45 | 375 | 468 | 335 | 507 | 467 |

[a]Absorption and
[b]PL emission maximum in THF solution (375 nm excitation).
[c]Absorption and
[d]PL emission maximum in films spin-coated from THF (310 nm excitation).
[e]PL emission maximum in films spin-coated from $CH_3CN$ (310 nm excitation).

Example 4b

Dilute, well solvated solutions of OPV amphiphiles in tetrahydrofuran (THF) showed absorption and PL emission at 375 nm and 467 nm, respectively, with no effect of PEG length. However, in spin-coated films the length of PEG segments had a significant effect on the $\lambda_{abs}$ of UV absorption. All films showed enhanced vibronic structure and an absorption blue-shift, indicating H-type aggregation with parallel alignment of the OPV transition dipole moments, consistent with a low tilt angle and no interdigitation of the OPV component segments within the bilayer smectic structure. This suggests two distinct OPV layers, separated by a PEG component layer, in which exciton coupling can occur between molecules within a layer, but not between adjacent layers. The longer the PEG block, the smaller the $\lambda_{abs}$ blue-shift, as crystallization of longer PEGs should disrupt the smectic layers thereby reducing OPV aggregation. Film PL depends on both solvent and PEG length, as observed by the PL emission maximum ($\lambda_{PL}$) of films spin-coated from $CH_3CN$, which shifts from 504 nm for OPV-16 to 468 nm for longer amphiphiles. In shorter OPV amphiphiles, aggregation and exciton coupling within the highly ordered OPV layer could explain the red-shifted $\lambda_{PL}$. At the same time, the structural disorder of the OPV induced by crystallization of longer PEGs can reduce aggregation and limit energy transfer between OPV chromophores, enhancing emission and leading to the observed PL spectra of OPV-45 films, which is almost identical to that of the molecule in dilute solution. It is at first counterintuitive that crystallization of one segment of the molecule (PEG) could increase disorder in another segment (OPV). However, this is consistent with the spectroscopic data, and is reasonable considering the very different crystal structures of the two separate portions of the molecule, which likely prevent the amphiphile from adopting a packing geometry that is simultaneously favorable for both PEG and OPV. Thus as the length of the PEG segment increases, its equilibrium structure appears to dominate, at least in the systems studied, the overall behavior of the amphiphile, at the expense of the highly ordered OPV-driven structure present in shorter amphiphiles.

Example 5

OPV-amphiphiles are soluble in most polar organic solvents and, for OPV-24 or longer, are soluble in water as well. At high concentration (>30 wt %), they form lyotropic LC phases that likely consist of a solvent swelled PEG layer and an aggregated OPV-alkyl layer. Based on the Israelachvili packing model that the bulky PEG chains of the longer amphiphiles can increase the curvature of the hydrophobic-hydrophilic interface, forming hexagonal or cubic mesophases. Only lamellar structures are observed however, possibly because OPV aggregation frustrates hydrophobic collapse, increasing the effective molecular cross-section at the interface.

Example 6

OPV-45 was used for study of lyotropic LC gels since longer PEGs imparted better solubility and more promising PL behavior. Table 3 details results of DSC and SAXS on this amphiphile in solvents where mesophase behavior was observed.

TABLE 3

Lyotropic LC Clearing Temperature and Lamellar Layer Spacing

| solvent[a] | $T_c$ (° C.) | $d_{100}$ (nm)[b] |
|---|---|---|
| $H_2O$ | >100 | 11.0 |
| DMSO | 68 | 11.1 |
| $CH_3CN$ | 55 | 11.3 |
| DMF | 52 | 13.1 |

[a]Mesophases formed with 40 wt % OPV-45 in the listed solvent.
[b]Layer spacing determined from first order diffraction peak in SAXS.

The concentration used corresponds to a water-PEG ratio of 1.9:1 (w/w) or 4.6 water molecules per PEG repeat unit. This should result in full hydration of PEG, with hydrogen bonding saturated and nearly all water in the bound state. As the solvent is largely immobilized, the mixture forms a highly viscous, transparent gel. The gels are strongly fluorescent despite the high concentration of OPV.

Example 7

Examining the PL of aqueous OPV amphiphile solutions, at low concentrations $\lambda_{PL}$ is 473 nm, showing a small solvatochromic shift from the 468 nm peak in THF (Table 2). PL intensity is directly proportional to concentration up to 0.1 wt %, beyond which a 30 nm red shift and exponential decrease in PL emission is observed, consistent with OPV aggregation above the critical micelle concentration (CMC) of the solution. A sharp shoulder appears at 505 nm, reaching a maximum at 10 wt % amphiphile, which could be vibronic in nature or due to J-aggregate formation. At 30 wt % LC mesophase formation induces a surprising change in the shape of the PL spectrum. The peak at 505 nm diminishes and the emission blue shifts toward that of dilute solutions, possibly due to confinement of the OPV within the layered LC structure, thus limiting intermolecular energy transfer.

Example 8

Lamellar LC order was confirmed in the aqueous OPV-amphiphile gel by POM and SAXS. On heating to 40° C., the LC phase aligns homeotropically on glass, likely due to strong interaction between PEG and the hydrophilic glass surface. The LC phase can also be oriented homogenously through shear induced alignment. Uniformly aligned regions several cm in diameter have been prepared, which is a significant improvement over thermotropic films where domain sizes are generally less than 100 μm (FIG. 2). This suggests a facile route to align OPV amphiphile films by casting from a dilute aqueous solution. As water evaporates, the molecules undergo a transition through an LC phase, yielding ordered, aligned films on drying. SAXS confirmed that lamellar structure of the aqueous gel is retained on drying, though the layer spacing increases from 11 to 15 nm. This likely is due to rearrangement of the PEG chain, which typically adopts a 7/2 helical conformation (7 monomer repeats units per 2 turns) on drying with a pitch of 1.93 nm, giving an expected length of 12.5 nm for OPV-45. Thus the observed length is consistent with a lamellar packing model with a fully interdigitated PEG layer.

Example 9

To confirm LC order contributes to the novel photoluminescence of OPV-amphiphile gels, its temperature dependence was examined. Aqueous gels remain in the LC phase up to the solvent's boiling point, thus the temperature dependence of PL was determined for a 40 wt % gel of OPV-45 in dimethylsulfoxide (DMSO) instead of water. At this composition, the amphiphile crystallizes at room temperature, forms a lamellar LC between 38° C. and 68° C. and an isotropic solution above. PL spectra for the DMSO gel at various temperatures shows a four-fold increase in PL intensity and a 25 nm blue shift occur on formation of the LC mesophase. On isotropization PL intensity returns to its previous level. The transition is fully reversible, and similar results were obtained in other solvents such as acetonitrile. While fluorescence varied significantly as a function of temperature, absorption did not, indicating that the observed behavior is not due to changes in scattering or absorption by the gel. Instead it appears that photoluminescence is enhanced due to the ordered structure of the lyotropic liquid crystal, which could alter the OPV's aggregation state or limit exciton coupling and migration within the OPV sublayers of the lamellar structure. The ability to control the nanoscale structure and aggregation of OPV through amphiphilic self-assembly, as demonstrated in these systems, may prove useful in enhancing the performance of phenylene vinylene-based molecules for a variety of organic electronics applications.

With regard to examples 10-15 unless otherwise noted, all starting materials were obtained from commercial suppliers and used without further purification. $^1$H NMR spectra were recorded on a Varian Unity 400 (400 MHz) spectrometer using the solvent proton signal as standard. UV-vis spectra were recorded on HP 8452 spectrometer. Fluorescence spectra were recorded on ISS PC1 Photon Counting Fluorometer. Film thickness of the samples was determined by applying Cauthy model to ellipsometric data in transparent region recorded on SOPRA MOSS ES4G spectroscopic ellipsometer. XRD patterns were recorded on a Rigaku RINT X-ray diffractometer. Infrared absorption spectra were recorded on Thermo Nicolet Nexus 870 FT-IR spectrometer.

Example 10

Amphiphiles IIIa-d were prepared by the following procedures (10a-g). Other such compounds can be synthesized by choice of other, longer alkanolamines.

Example 10a

ω-((Dimethylamino)alkyl)-methanesulfonate hydrochloride (7a and 7b). N,N-Dimethylpropanolamine (4.13 g, 40 mmol, 1 equiv.) was dissolved in 100 mL of $CH_2Cl_2$ and the solution was cooled down to 0° C. Methanesulfonyl chloride (3.7 mL, 48 mmol, 1.2 equiv.) was added slowly and the mixture was stirred for 24 h at r.t. White precipitate was filtered out and dried in vacuo to afford the product 7b (8.42 g, 97% yield). $^1$H NMR (DMSO-$d_6$) δ10.78 (s, 1H), 4.30 (t, 2H, J=5.0 Hz), 3.22 (s, 3H), 3.11 (t, 2H, J=6.0 Hz), 2.73 (s, 6H), 2.08 (m, 2H).

Example 10b 4-(ω-(dimethylamino)alkoxy)-benzaldehyde (8a and 8b). 4-Hydroxybenzaldehyde (4.73 g, 38.7 mmol, 1 equiv.), 7b (8.42 g, 38.7 mmol, 1 equiv.), potassium carbonate (21.4 g, 155 mmol, 4 equiv.) and 18-crown-6-ether (0.95 g, 3.87 mmol, 0.1 equiv.) were placed in a flask with a magnetic stirring bar and a cooling column, and dissolved in 200 ml of acetone. The mixture was refluxed for 24 h. After cooling down, the mixture was filtrated and concentrated in vacuo.

The crude product was subjected to a column chromatography using 5% MeOH/CH$_2$Cl$_2$ to afford the product 8b as clear oil (4.47 g, 56%) $^1$H NMR (CDCl$_3$) δ9.87 (s, 1H), 7.82 (d, 2H, J=8.8 Hz), 7.00 (d, 2H, J=8.2 Hz), 4.10 (t, 2H, J=6.4 Hz), 2.46 (t, 2H, J=7.1 Hz), 2.25 (s, 6H), 1.99 (m, 2H).

Example 10c 4-(ω-Bromoalkoxy)-benzaldehyde (9c and 9d). 4-Hydroxybenzaldehyde (1.22 g, 10 mmol, 1 equiv.), 1,6-dibromohexane (3.7 g, 15 mmol, 1.5 equiv.), potassium carbonate (2.8 g, 20 mmol, 2 equiv.) and 18-crown-6-ether (0.25 g, 1 mmol, 0.1 equiv.) were placed in a flask with a magnetic stirring bar and a cooling column, and dissolved in 200 ml of acetone. The mixture was refluxed for 24 h. After cooling down, the mixture was filtrated and concentrated in vacuo. The crude product was subjected to a column chromatography using CH$_2$Cl$_2$ to afford the product 9d as clear oil (1.7 g, 60%) $^1$H NMR (CDCl$_3$) δ9.88 (s, 1H), 7.83 (d, 2H, J=8.6 Hz), 6.98 (d, 2H, J=8.5 Hz), 4.05 (t, 2H, J=6.5 Hz), 3.43 (t, 2H, J=6.8 Hz), 1.90 (m, 2H), 1.83 (m, 2H), 1.53 (m, 4H).

Example 10d 4-(ω-(dimethylamino)alkoxy)-benzaldehyde (8c and 8d). Dimethylamine solution (18 mL, 34.5 mmol, 2.0 M in THF, 5 equiv.) was added to 9c (1.78 g, 6.9 mmol, 1 equiv.) at r.t. and stirred for 24 h to give a white suspension. The reaction mixture was washed with H$_2$O/CH$_2$Cl$_2$ and organic layer was dried and evaporated. The crude product was subjected to a column chromatography using 5% MeOH/CH$_2$Cl$_2$ to afford the product 8c as yellow solid (1.93 g, 61% yield). $^1$H NMR (CDCl$_3$) δ9.87 (s, 1H), 7.82 (d, 2H, J=8.6 Hz), 6.98 (d, 2H, J=8.6 Hz), 4.06 (t, 2H, J=6.4 Hz), 2.36 (m, 2H), 2.26 (m, 6H), 1.84 (m, 2H), 1.67 (m, 2H).

Example 10e

Tetraethyl p-xylylenediphosphonate (9). α, α'-Dibromo-p-xylene (5.28 g, 20 mmol, 1 equiv.) and triethyl phosphite (10.3 mL, 60 mmol, 3 equiv.) were placed in a flask with a magnetic stirring bar. A distillation apparatus was attached to collect ethyl bromide formed along with the reaction. The mixture was immersed in an oil bath and heated to 130° C. for 2 h. After cooling down, white crystal crushed out and recrystalized from hexane to give the product (6.74 g, 89% yield). $^1$H NMR (CDCl$_3$) δ7.24 (s, 4H), 4.00 (m, 8H), 3.12 (d, 4H, J=20.2 Hz), 1.23 (t, 12H, J=7.0 Hz).

Example 10f 1,4-bis(2-(4-(ω-(Dimethylamino)alkoxyphenyl))-(E)-1-ethenyl)benzene (10). Compounds 9 (0.72 g, 1.91 mmol, 1 equiv.) and 8c (0.93 g, 4.2 mmol, 2.2 equiv.) were dissolved in 100 mL of THF and cooled down to 0° C. t-BuOK solution (10 mL, 10 mmol, 1.0 M in t-BuOH) was slowly added to the solution with stirring. The reaction mixture was stirred overnight at room temperature, and quenched by adding excess amount of water. White solid precipitated out was collected by filtration and recrystalized from CHCl$_3$/hexane to afford the product 10c as pale yellow solid (0.72 g, 74% yield). $^1$H NMR (CDCl$_3$) δ7.47 (m, 8H), 7.07 (d, 2H, J=16.1 Hz), 6.96 (d, 2H, J=16.3 Hz), 6.89 (d, 4H, J=8.2 Hz), 4.00 (t, 4H, J=6.0 Hz), 2.33 (t, 4H, J=7.3 Hz), 2.24 (s, 12H), 1.82 (m, 4H), 1.65 (m, 4H).

Example 10g 1,4-bis(2-(4-(ω-(Trimethylammonium)alkoxyphenyl))-(E)-1-ethenyl) benzene dibromide. To a suspension of 10c (0.5 g, 0.98 mmol, 1 equiv.) in 100 mL of THF, MeBr solution (5 mL, 10 mmol, 2.0 M in t-BuOMe) was added at room temperature. The mixture was stirred overnight and white solid was collected by filtration to afford the product IIIc as pale yellow solid (0.69 g, 100% yield). $^1$H NMR (DMSO-d$_6$) δ7.54 (m, 8H), 7.21 (d, 2H, J=16.4 Hz), 7.08 (d, 2H, J=16.4 Hz), 6.95 (d, 2H, J=8.47 Hz), 4.04 (t, 4H, J=5.5 Hz), 3.35 (m, 4H), 3.06 (s, 9H), 1.81 (m, 4H), 1.73 (m, 4H).

Example 11

Figure 3:
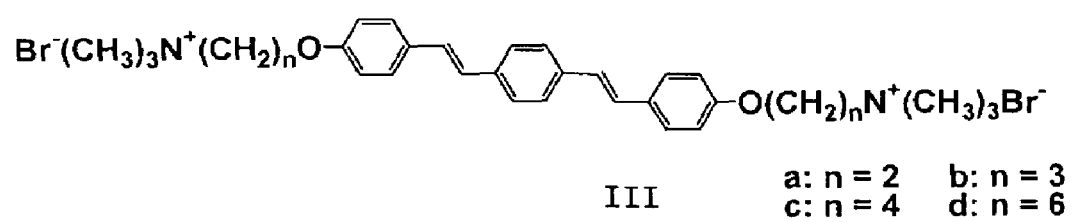
FIG. 3 shows a general structural formula representing various, non-limiting embodiments of compound III, and Rhodamine B modified for silicate incorporation and demonstration of OPV energy transfer.
Figure 3:
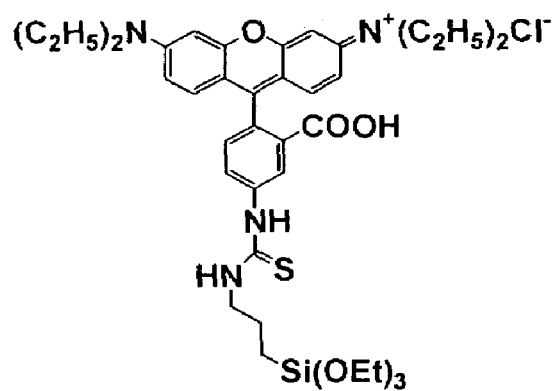

Rhodamine B derivative attached silicate precursor. Rhodamine B isothiocyanate (5.36 mg, 1×10$^{-5}$ mol, 1 equiv) was dissolved in anhydrous MeOH in a dried 5 mL volume flask. 3-Aminopropyltriethoxysilane (1.9 μL, 1.1×10$^{-5}$ mol, 1.1 equiv) was added to the solution at r.t. to afford 2 mM MeOH solution of the silicate precursor. (See, FIG. 3 and example 15, below.)

Example 12

OPV amphiphile/silicate hybrid films were prepared by first dissolving 6.0 mg of OPV IIIa (9.0×10$^{-6}$ mol) in 0.75 mL of MeOH and adding 15 μL of 35 wt % HCl and 14 μL of tetraethyl orthosilicate (TEOS, 6.25×10$^{-5}$ mol). The final reactant molar ratios in the solution were: 1 TEOS:0.15 OPV:300 MeOH:8.3H$_2$O:2.5 HCl. The solution was stirred for 0.5 h at room temperature. The addition of HCl induces the hydrolysis of TEOS and charged silicate oligomers are expected to interact with the hydrophilic segment of the molecules. The solution was membrane filtered (pore size: 0.45 μm) and deposited on a quartz or silicon substrate by spin-casting at 500-3000 rpm. The films were left overnight at ambient atmosphere and subsequently dried in vacuo for 3 h. Uniform and transparent films with thickness of 40-80 nm were obtained and characterized as on the substrates with various techniques.

The X-ray diffraction (XRD) patterns of IIIa/silicate films spin-cast at 1000 rpm showed a peak at 2.6 nm, suggesting the presence of a periodic structure in the hybrid film perpendicular to the substrate. This value is close to the length of one molecule along the long axis (calculated distance between two nitrogens is 2.5 nm). Using OPV amphiphiles with n=3 (IIIb) and n=4 (IIIc), the d-spacings of the films increased to 3.0 nm and 3.3 nm, respectively. The OPV amphiphile with n=6 (IIId) gave an inhomogeneous, opaque film because of its low solubility in MeOH. The detailed nature of the periodic structure is not clear, but possibly hexagonal or disordered layered structure. Detailed X-ray analysis is now under investigation.

Example 13

In order to determine the molecular orientations in the film, infrared (IR) transmittance spectra were taken of IIIa/silicate films deposited on undoped silicon substrates. Peaks at 1602 cm$^{-1}$ and 962 cm$^{-1}$ are assigned to the vibrational modes of OPV corresponding to phenyl ring quadrant stretching (parallel to the axis of 1,4-substitution) and trans vinyl C—H out of plane wagging (perpendicular to the phenyl plane), respectively. The orientation of phenyl rings of OPV in the film is calculated by comparing the ratio of the areas under the peaks at 1602 cm$^{-1}$ and 962 cm$^{-1}$ to that of an isotropic sample. An order parameter of 0.25 was obtained, which indicates a weak orientation of the molecules along the surface normal in IIIa/silicate films.

Example 14

The UV-vis absorption spectra of IIIa/silicate films showed a broad peak with a maximum at 350 nm, with a blue shift compared with that of IIIa in MeOH (362 nm). This shift could be attributed to the aggregation of OPV segments in the film, which is further supported by fluorescence spectra. The maximum in the excitation spectra of the films (356 nm) showed a slight blue shift compared with IIIa in MeOH (362 nm), while the emission spectra of the films showed a red shift from 420 nm to 450 nm.

Based on the spectroscopic observations, the OPV segments of IIIa are believed to stack into H-aggregates held together by π-π interaction with the weak orientation of the molecular long axis perpendicular to the substrate. The silicate formed through the hydrolysis of TEOS should interact with the hydrophilic segment of the molecules and segregate the OPV aggregates.

Example 15

In order to investigate the effect of the ordered structure and the molecular orientation on energy transfer, IIIa/silicate films were prepared, doped with rhodamine B isothiocyanate derivative (see FIG. 3 and example 11) as an energy acceptor. By introducing a triethoxysilane group, the dye, is expected to incorporate into the silicate network. XRD patterns confirmed that the dye was incorporated in the films up to 5 mol % of IIIa without disrupting the periodic structure. As a control sample, poly(2-hydroxyethyl methacrylate) (PHEMA) was used as a matrix to fabricate a film with a random orientation of IIIa with the same concentration. IIIa/PHEMA films were prepared by spin-casting an acidic precursor solution similar to the silicate films, except that 10 mg of PHEMA is used instead of TEOS. When the films doped with 2 mol % of the dye were excited at 350 nm (OPV absorbs at the wavelength but the dye does not), quenching of fluorescence from IIIa at 450 nm and emission from the dye at 620 nm were observed. Interestingly, the red fluorescence from the dye in IIIa/silicate films were much stronger than in IIIa/PHEMA, suggesting enhanced energy transfer in IIIa/silicate films. Although it has been recently reported that gelation of OPV based materials induces enhancement of energy transfer to rhodamine B dye, the use of a 5-fold excess of dye molecules to OPV is needed in the gel to achieve sufficient energy transfer, while only 2 mol % doping is needed in our ordered silicate films.

This enhancement of the fluorescence from the dye in IIIa/silicate films could be attributed to several factors: (1) more uniform dispersion of the dye in silicate than in PHEMA; (2) larger spectral overlap between emission of IIIa and excitation of the dye in IIIa/silicate films; (3) shorter mean distance between excited state of IIIa and the dye because of efficient energy migration between IIIa molecules within segregated OPV domains. Dynamic fluorescence study on the films would give us information on these possibilities.

As shown above, in examples 1-9, amphiphilic molecules comprising OPV trimer end-substituted asymmetrically, with a hydrophobic alkyl chain and a hydrophilic ethylene glycol chain, can self-assemble forming both thermotropic and lyotropic liquid crystalline mesophases. By varying the length of the ethylene glycol block, one can change the structure and solubility of the amphiphile, altering its optoelectronic properties. Photoluminescence from films of the amphiphile with the longest hydrophilic chain resembles that of molecules in dilute solution, indicating that self-assembly dramatically alters the aggregation behavior of the OPV chromophore. The layered LC phase appears to inhibit OPV aggregation and reduce exciton migration, leading to enhanced and blue-shifted photoluminescence. Formation of ordered OPV-amphiphile mesophases provides a facile route to prepare nanostructured films in which the structural and optical properties are controlled to a degree not possible with soluble PPV polymers or other substituted OPVs of the prior art.

Alternatively, as shown in examples 10-15, the fabrication of novel nanostructured OPV/silicate hybrid films can be achieved by one-step deposition. Fluorescence studies showed enhanced energy transfer between OPV and rhodamine B derivative incorporated into silicate network. Considering the luminescence properties of OPV, using such nanostructures in LEDs would provide an efficient approach to control the electron/energy transport processes in those devices.

We claim:

1. A compound of a formula

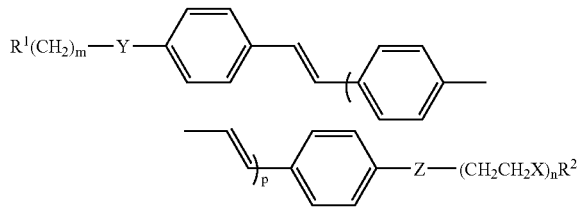

wherein Y and Z are independently selected from O, NH, C(O)O and C(O)NH, and X is selected from O and $CH_2$; and wherein $R^1$ and $R^2$ are quaternary ammonium salt moieties where X is $CH_2$ and at least one of Y and Z is not O; n is an integer ranging from 2 to about 50; m is an integer ranging from 2 to about 20; and p is an integer ranging from 1 to about 4.

2. The compound of claim 1 wherein X is O, n ranges from about 8 to about 24, and $R^1$ and $R^2$ are independently selected from H and alkyl moieties.

3. The compound of claim 2 wherein p is 1 and n is about 6 to about 12.

4. The compound of claim 2 in a fluid medium, said medium selected from a polar solvent, a non-polar solvent and combinations of said solvents, contacted with a substrate and fabricated on said substrate upon fluid evaporation.

5. The compound of claim 1 wherein X is $CH_2$, and n and m independently range from 2 to about 6.

6. The compound of claim 5 wherein p is 1.

7. The compound of claim 5 in a fluid medium, said medium selected from a polar solvent, a non-polar solvent and combinations of said solvents, contacted with a substrate and fabricated on said substrate upon fluid evaporation.

8. A composition comprising a compound of a formula

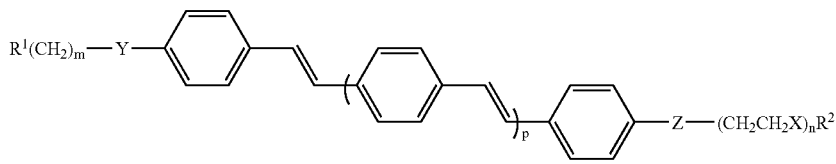

wherein Y and Z are independently selected from O, NH, C(O)O and C(O)NH, and X is selected from O and $CH_2$; and wherein $R^1$ and $R^2$ are quaternary ammonium salt moieties where X is $CH_2$ and at least one of Y and Z is not O; n is an integer ranging from 2 to about 50; m is an integer ranging from 2 to about 20; and p is an integer ranging from 1 to about 4.

9. The composition of claim 8 wherein X is O and n ranges from about 8 to about 24.

10. The composition of claim 9 comprising a liquid crystalline phase of said compound.

11. The composition of claim 9 comprising a substrate.

12. The composition of claim 8 wherein X is $CH_2$, and n and m independently range from 2 to about 6.

13. The composition of claim 12 comprising the condensation product of said compound and a silicate.

14. The composition of claim 13 comprising a substrate.

15. A compound of formula

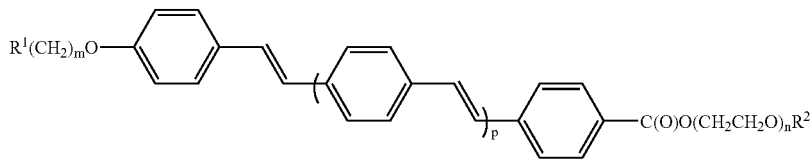

wherein n is an integer ranging from 2 to about 50; m is an integer ranging from 2 to about 20; p is an integer ranging from 1 to about 4; and $R^1$ and $R^2$ are independently selected from H and alkyl moieties.

16. The compound of claim 15 wherein p is 1 and n ranges from about 6 to about 12.

17. A condensation product of an oligomeric silicate and a compound of a formula

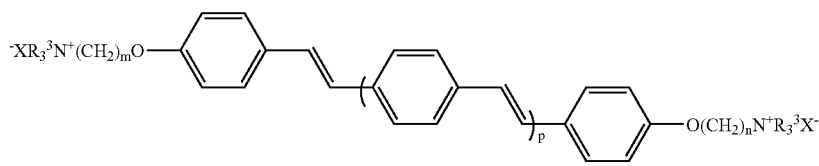

wherein m and n are integers independently ranging from 2 to about 20, $R^3$ is independently selected from H and alkyl moieties; X is a counter ion; and p is an integer ranging from 1 to about 4.

18. The compound of claim 17 wherein $R^3$ is alkyl, X is halide, and p is 1.

19. A method of using amphiphilicity of an oligo(phenylene vinylene) to induce molecular structure, said method comprising:

providing a compound of a formula

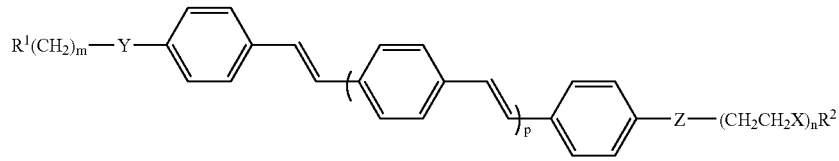

wherein X is selected from O and $CH_2$, and $R^1$ and $R^2$ are independently selected from H and alkyl moieties where X is O, and $R^1$ and $R^2$ are quaternary ammonium salt moieties where X is $CH_2$, Y and Z are independently selected from O, NH, C(O)O and C(O)NH; n is an integer ranging from 2 to about 50; m is an integer ranging from 2 to about 20; and p is an integer ranging from 1 to about 4;

contacting an amphiphilic component of said compound with a medium selected from a fluid and a silicate.

20. The method of claim 19 wherein X is O and n is varied from about 8 to about 24.

21. The method of claim 20 wherein said medium is a fluid selected from a polar solvent, a non-polar solvent and combinations of said solvents.

22. The method of claim 21 further comprising fabrication of said compound on a substrate.

23. The method of claim 19 wherein X is $CH_2$, and m and n are independently varied from about 2 to about 6.

24. The method of claim 23 wherein said medium is a silicate.

25. The method of claim 24 further comprising fabrication of said compound on a substrate.

* * * * *

UNITED STATES PATENT AND TRADEMARK OFFICE
CERTIFICATE OF CORRECTION

PATENT NO. : 7,371,887 B2
APPLICATION NO. : 11/005558
DATED : May 13, 2008
INVENTOR(S) : Samuel I. Stupp et al.

It is certified that error appears in the above-identified patent and that said Letters Patent is hereby corrected as shown below:

Title page; item [75] Inventor "Keisuke Tajima, Evanston, IL (US)" should be
-- Keisuke Tajima, Tokyo, Japan --

Signed and Sealed this

Twenty-fifth Day of November, 2008

JON W. DUDAS
*Director of the United States Patent and Trademark Office*